(12) United States Patent
Benvegnu et al.

(10) Patent No.: US 8,088,747 B2
(45) Date of Patent: Jan. 3, 2012

(54) ANALOGUE COMPOUNDS OF ARCHAEBACTERIAL MEMBRANE LIPIDS AND LIPOSOMAL COMPOUNDS INTEGRATING SUCH COMPOUNDS

(75) Inventors: Thierry Benvegnu, Rennes Cedex (FR); Daniel Plusquellec, Noval Chatillon sur Seiche (FR); Gildas Rethore, Redon (FR); Mickaelle Scahet, Le Mans (FR); Claude Ferec, Plougastel-Deaoulas (FR); Tristan Montier, Brest (FR); Pascal Delepine, Bohard (FR); Pierre Lehn, Brest (FR)

(73) Assignees: Ecole Nationale Superieure de Chime de Rennes, Cedex (FR); Universite de Bretagne Occidentale, Cedex (FR)

( * ) Notice: Subject to any disclaimer, the term of this patent is extended or adjusted under 35 U.S.C. 154(b) by 663 days.

(21) Appl. No.: 11/792,011

(22) PCT Filed: Dec. 7, 2005

(86) PCT No.: PCT/EP2005/056555
§ 371 (c)(1),
(2), (4) Date: Apr. 8, 2008

(87) PCT Pub. No.: WO2006/061396
PCT Pub. Date: Jun. 15, 2006

(65) Prior Publication Data
US 2009/0232880 A1 Sep. 17, 2009

(30) Foreign Application Priority Data
Dec. 7, 2004 (FR) ..................................... 04 13028

(51) Int. Cl.
*A61K 31/7105* (2006.01)
*A61K 31/711* (2006.01)
*A61K 9/127* (2006.01)
*C07C 35/06* (2006.01)
*C07C 43/115* (2006.01)

(52) U.S. Cl. ........ 514/44 R; 424/420; 568/670; 568/838
(58) Field of Classification Search .................... None
See application file for complete search history.

(56) References Cited

FOREIGN PATENT DOCUMENTS
WO   WO97/22333   6/1997
WO   WO00/64858   11/2010

OTHER PUBLICATIONS

Benvegnu, et al. (2004) "Archaeosomes Based on Novel Synthetic Tetraether-Type Lipids for Developement of Oral Delivery Systems", Current Opinion in Colloid and Interface Science, 8(6): 469-79.*
Benvegnu, et al. (Online Oct. 10, 2005) "Archaeosomes Based on Novel Synthetic Tetraether-type Lipids for the Development of Oral Delivery Systems", Chemical Communications, 5536: 5536-5538.*
International Search Report.
De Rosa, Maria, "Archael Lipids: Structural Features and Supramolecular Organization" Thin Solid Films 284-285 (1996) 13-17.
De Rosa, Archaeal lipids: Structural Features and supramolecular organization, Thin Solid Films, Elsevier-Sequoia, S. A. Lausanne, CH, vol. 284-285, Sep. 15, 1996, pp. 13-17, XP004078130, ISSN: 0040-6090, pp. 13-15, dolonne de gauche, figure 1, p. 16, colonne de droite.
Seelmann, M.; International Preliminary Report on Patentability, dated Jul. 12, 2005.
De Rosa, Archaeal lipids: Structural Features and supramolecular organization, Thin Solid Films, Elsevier-Sequoia, S.A. Lausanne, CH, vol. 284-285, Sep. 15, 1996, pp. 13-17, XP004078130, ISSN: 0040-6090, pp. 13-15, dolonne de gauche, figure 1, p. 16, colonne de droite.
Author Unknown; In vivo Liposome Transfection Reagent 20 mM DOTAP: Cholesterol (1:1 molar ratio) extruded liposomes in 5% glucose; SIGMA; Product No. L 6910; Product Information, Date: Jan. 2011.

* cited by examiner

*Primary Examiner* — Robert M Kelly
(74) *Attorney, Agent, or Firm* — Thomas, Kayden, Horstemeyer & Risley, LLP

(57) ABSTRACT

The invention relates to a compound of general formula (I): where X=0 or 1, Z=O, S or $CH_2$, $R_1$ and $R_2$ independently=OH or OY, where Y=a protecting group, $OR_3$, where $R_3$=a monosaccharide or disaccharide group, $A_1$-$CH_2$—$N^+(CH_3)_3$, X', where X=halogen, $A_1$=an amide (NHC(O)) or ester (OC(C)) bond, $OPO(OM)_2$, where M=an alkyli or alkyli earth metal, $OP(O)O^-$—$O(CH_2)_2$—$N^+(CH_3)_3$, $A_2$-$(PEG_{X_1}$-$A_3)_n$-$R_4$, where n=0 or 1, $PEG_{X_1}$=a polyethyleneglycol of molecular weight $X_1$, where $X_1$ being less than or equal to 5,000 daltons, $A_2$ and $A_3$ independently=a ether (O), ester (OC(O)), amide (NHC(O)), urea (NHC(O)NH), thiourea (NHC(S)NH), or thioether (S) bond $R_4$=a directing agent.

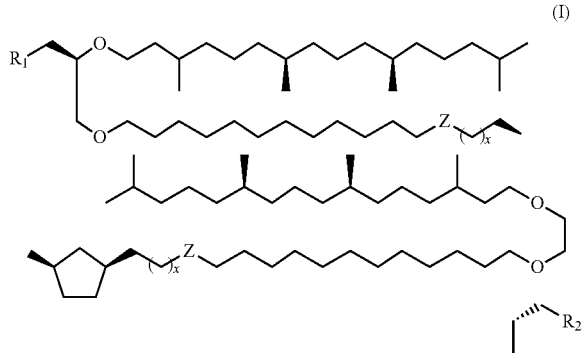

21 Claims, 2 Drawing Sheets

ANALOGUE COMPOUNDS OF ARCHAEBACTERIAL MEMBRANE LIPIDS AND LIPOSOMAL COMPOUNDS INTEGRATING SUCH COMPOUNDS

The present invention concerns the pharmaceutical field.

More specifically, the invention concerns new synthetic analogue compounds of archaebacterial membrane lipids.

The invention also concerns new liposomal compositions utilizing such compounds as well as the use of such compositions to provide a delivery system for molecules of therapeutic interest and/or to provide a delivery system for RNA or DNA molecules.

The development of high-performance systems for administering and transporting a biologically active molecule up to its biological target constitutes a major issue. In fact, no medicine can be therapeutically active if the active substance it contains is not capable of crossing the biological barriers that separate the site of administration from the site of action.

Liposomes are, however, positioned as promising candidates in this field and their recent introduction into the therapeutic arsenal in cancerology and infectology represents the result of considerable effort in research and development.

Nevertheless, several problems remain particularly if one considers the oral or intravenous routes of administration via the oral route or the blood route. These problems are related to the instability of the liposome in vivo in acid milieus such as, for example, that observed in the stomach which has a pH of 2, and/or upon destabilisation of the liposomal wall by interaction with blood proteins and lipoproteins.

One possible approach for improving the properties of these formulations consists of using the bipolar lipids of thermophilic and methanogenic archaebacteria which have increased stability compared to conventional liposomes. For this reason, these have interesting potential applications as vectors of active ingredients and therapeutic genes or as administration systems for vaccines.

However, the culture, extraction and purification techniques currently do not allow for large quantities of natural lipids to be obtained. The preparation of liposomes from synthetic lipids with perfectly defined structures is thus an interesting alternative.

One objective of the present invention is to propose archaebacterial lipid membrane analogues with a lipophilic spacer that has a length comparable to that of natural molecules.

Another objective of the present invention is to describe new liposomal compositions integrating such analogues.

These objectives are reached thanks to the invention, which concerns compounds with the general formula (1):

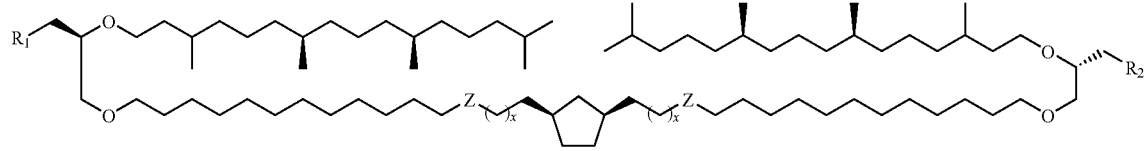

in which:
X is equal to zero or one;
Z represents an O, an S or a $CH_2$;
$R_1$ and $R_2$, which can be identical or different, represent one of the following substituents:
OH
OY with Y representing a protector group, preferentially an allyl, benzyl, tetrahydropyranyl, or trialkylsilyl groups;
$OR_3$, $R_3$ representing a monosaccharide or disaccharide substituent;

$OPO(OM)_2$, M representing a metal cation or alkaline-earth metal;
$A_1$-$CH_2$—$N^+(CH_3)_3$, $X^-$, X representing a halogen, $A_1$ representing an amide (NHC(O)) or ester (OC(O)) bond.

According to an interesting variant of the invention, the compounds according to the invention present $R_1$ and $R_2$ substituents identical or equal to $OR_3$, $R_3$ being a β-lactosyl.

According to another interesting variant of the invention, the compounds according to the invention present substituents $R_1$ and $R_2$ identical and equal to $OP(O)O^-$—$O(CH_2)_2$—$N^+(CH_3)_3$.

$A_1$-$CH_2$—$N^+(CH_3)_3$, $X^-$, X representing a halogen, $A_1$ representing an amide (NHC(O)) or ester (OC(O)) bond;
$OPO(OM)_2$, M representing an alkaline metal cation or alkaline-earth metal;
$OP(O)O^-$—$O(CH_2)_2$—$N^+(CH_3)_3$,
$A_2$-$(PEG_{X1}$-$A_3)_n$-$R_4$, n being equal to 0 or 1, $PEG_{X1}$ being a polyethyleneglycol of molecular weight $X_1$, $X_1$ being less than or equal to 5,000 daltons, $A_2$ and $A_3$ being identical or different and representing one ether (O), ester (OC(O)), amide (NHC(O)), urea (NHC(O)NH), thiourea (NHC(S)NH), or thioether (S) bond, $R_4$ representing a targeting agent.

The hemimacrocyclic compounds with the general formula (1) according to the present invention are characterised by:
a hemimacrocyclic lipophilic skeleton comprising a spacer including a 1,3-disubstituted cyclopentane motif in the middle of the lipophilic chain and two ramified chains derived from phytanol, the cumulative length of which corresponds to that of the spacer and
two identical or different, neutral, anionic, cationic or zwitterionic polar heads.

The compounds according to the present invention are notably characterised by the novel presence of a cyclopentane motif in their formula.

Preferentially, when the compounds according to the present invention integrate a targeting agent, it is best chosen from the group constituted of folic acid, multi-antenna structures comprising several $R_3$ motifs, antibodies, and peptides; these ligands being specifically recognised by the corresponding membrane receptors: folate receptors for folic acid, the integrins for DGR peptides, and the lectins for the glycoconjugates.

It is also preferable that when the compounds according to the present invention integrate an $R_3$ substituent, it is best chosen from the group constituted of D-galactosyl, D-glucosyl, D-mannosyl, lactosyl, and maltosyl substituents.

It is also preferable that, the compounds according to the present invention conform to the general formula (1) in which:
x is equal to zero or one;
Z represents an O or a $CH_2$;
$R_1$ and $R_2$ are identical or different and represent one of the following substituents:
OH
$OR_3$, $R_3$ representing a lactosyl substituent;
$OP(O)O^-$—$O(CH_2)_2$—$N^+(CH_3)_3$;

According to another interesting variant of the invention, the compounds according to the invention present substituents $R_1$ and $R_2$ identical and equal to $NHC(O)CH_2-N^+(CH_3)_3$, $X^-$, X representing a halogen.

The present invention notably covers diols of formulas (1) and (2).

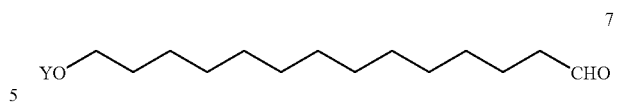

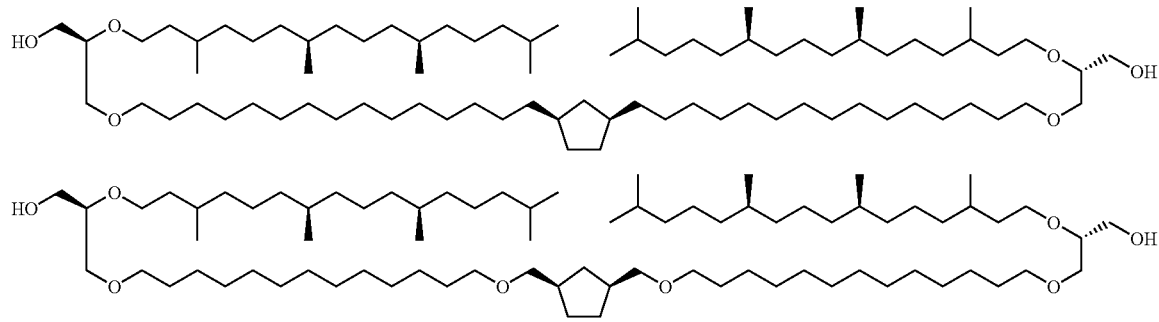

The present invention also covers the spacers with formulas (3) and (4) which can be used for the synthesis of the compounds mentioned above.

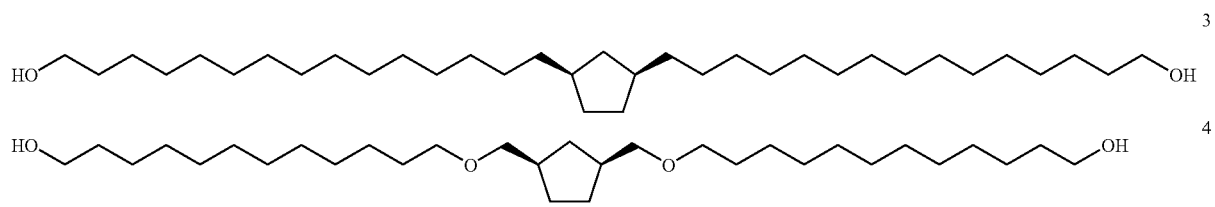

This synthesis may be achieved by different routes known to a person skilled in the art.

Concerning the compounds in which Z is equal to $CH_2$ or to O, this synthesis may comprise a first step consisting of coupling the spacers with formulas (3) and (4) and the chiral synthon of formula (5)

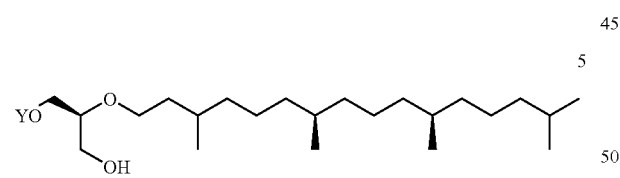

in which Y represents a benzyl, allyl, tetrahydropyranyl or trialkylsilyl protector group.

The spacer with formula (3) may be prepared according to a procedure which consists of creating two simultaneous C=C double bonds by a double Wittig reaction in one single container using phosphonium diiodine with formula (6)

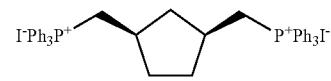

and the aldehyde with formula (7)

in which Y represents a benzyl, allyl, tetrahydropyranyl or trialkylsilyl protector group.

The phosphonium diiodine with formula (6) is prepared in two steps from cis-1,3-bis(hydroxymethyl)cyclopentane with the formula (8)

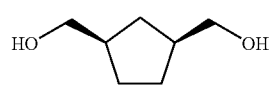

via an iodation reaction followed by nucleophilic substitution with triphenylphosphine.

After the double Wittig reaction, the deprotection of hydroxyl groups and reduction of double bonds formed leads to the spacer with formula (3).

The spacer with formula (4) may be prepared according to a procedure which consists of performing double alkylation between the triflate (or the mesylate, the para-toluene sulfonate or the corresponding halides) with formula (9) and diol (8)

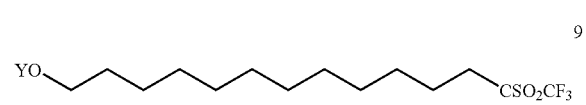

in which: Y represents a benzyl, allyl, tetrahydropyranyl or trialkylsilyl protector group.

The triflate with formula (9) is prepared by action of triflic anhydride in the presence of 2,6-lutidine from the alcohol with formula (10) in which Y represents a benzyl, allyl, tetrahydropyranyl or trialkylsilyl protector group.

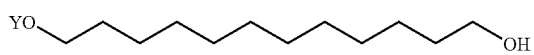

10

The di-O-alkylation reaction between the triflate (9) and the diol (8) is done in dichloromethane at reflux in the presence of 1,8-bis-(dimethylamino)-naphthalene. After di-O-alkylation, the elimination of Y protector groups results in the spacer with formula (3).

After reaction of spacers (3) and (4) with the synthon with formula (5), the Y protector groups are eliminated to make diols (1) and (2).

The last step then consists, if the case arises, in simultaneously or sequentially grafting one or two hydrophilic groups according to the character of symmetry sought, either symmetrical ($R_1=R_2$) or dissymmetrical ($R_1$ different from $R_2$) compounds with the general formula (1).

Access to symmetrical β-lactosylated compounds in which $R_1$ and $R_2$ are identical and equal to $OR_3$, $R_3$ being a β-lactosyl, is based on a bisglycosylation reaction of diols with formulas (2) and (3) from peracetylated thiolactosyl with formula (11).

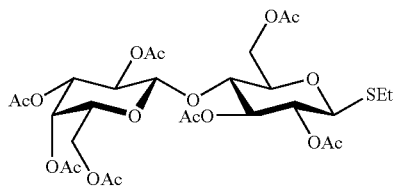

This is done under standard activation conditions (N-iodosuccinimide (NIS), triethylsilyl triflate ($Et_3SiOTf$), dichloromethane), followed by deacetylation of the disaccharide hydroxyls according to the Zemplen procedure ($CH_3ONa$, $CH_3OH$).

The compounds in which $R_1$ and $R_2$ are identical to $OR_3$, $R_3$ being a mannosyl or galactosyl substituent, are prepared under similar conditions.

The symmetrical compounds in which $R_1$ and $R_2$ are phosphatidylcholines ($R_1=R_2=OP(O)O^-$—$O(CH_2)_2$—$N^+(CH_3)_3$) are obtained in two steps by reaction between bromoethyldichlorophosphatate $Cl_2P(O)O$ —$(CH_2)_2$—Br and diols with formulas (2) and (3) in the presence of triethylamine, followed by reaction of the trimethylamine with the bromophosphate derivatives thus obtained ($R_1=R_2=OP(O)O^-$— $(CH_2)_2$—Br).

The symmetrical compounds with the general formula (1) in which $R_1$ and $R_2$ are betaines ($R_1=R_2=NHC(O)CH_2$—$N^+(CH_3)_{3+}X^-$, X representing a halogen), preferably linked to the lipophilic segment via amide bonds, are obtained by coupling the diamine (12) and the glycine betaine in active form (acylchloride (13) or thiazolidine-2-thione (14)) in the presence of triethylamine in dichloromethane.

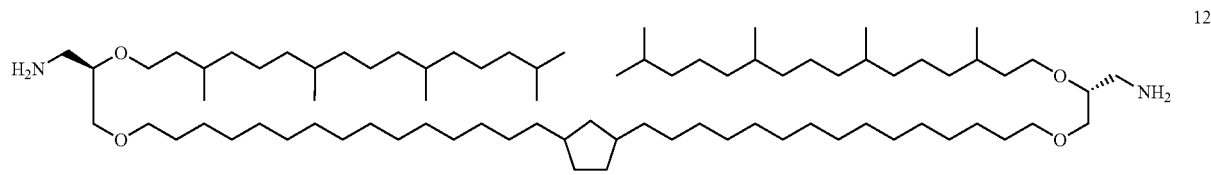

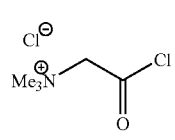

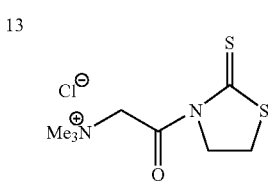

The dissymmetrical compounds with the general formula (1), with two different polar heads R₁ and R₂, are prepared according to a procedure which consists of breaking the symmetry of the diols from formulas (1) and (2) by the introduction of a benzyl group (or another analogous protector group) to yield alcohols with formulas (15) and (16):

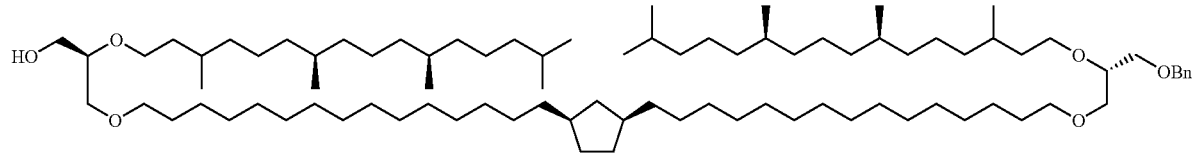

15

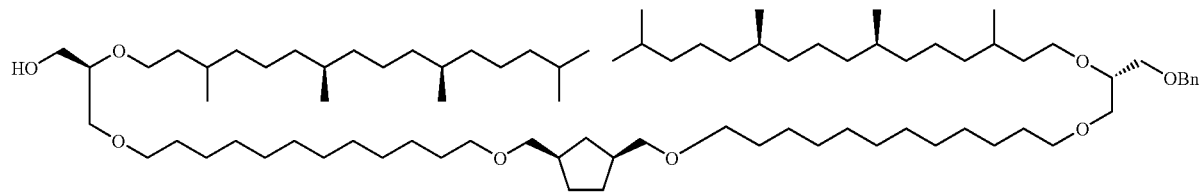

16

This mono-protection of diols with formulas (1) and (2) is preferentially done by the action of benzyl bromide (BnBr) in the presence of silver oxide (Ag₂O) in dichloromethane. At this stage, a first polar head is introduced at the free hydroxyl; then, with hydrogenolysis, the second head is incorporated. The final elimination of protector groups present at the polar heads leads to the target dissymmetrical structures.

The invention also concerns liposomal compositions incorporating at least one compound with the general formula (1) according the invention described above alone or mixed with one or several synthetic or natural colipids.

The compounds according the invention confer greater stability upon such liposomal compositions, especially in an acid milieu and with respect to blood proteins and lipoproteins.

The invention notably, but not exclusively, concerns such liposomal compositions in which the colipid is phosphatidylcholine from egg lecithin.

The invention also concerns such liposomal compositions containing at least one compound with the general formula (I) in which R₁ and R₂ are identical or different and represent one of the following motifs:

A₁-CH₂—N⁺(CH₃)₃, X⁻, X representing a halogen, A₁ representing an amide (NHC(O)) or ester (OC(O)) bond;

A₂-(PEG$_{X1}$-A₃)$_n$-R₄, n being equal to 0 or 1, PEG$_{X1}$ being a polyethyleneglycol of molecular weight X₁, X₁ being less than or equal to 5,000 daltons, A₂ and A₃ being identical or different and representing one ether (O), ester (OC(O)), amide (NHC(O)), urea (NHC(O)NH), thiourea (NHC(S)NH), or thioether (S) bond, R₄ representing a targeting agent;

and at least one cationic colipid, and at least one fusogenic colipid.

The cationic colipid may, for example, be a two-chain cationic lipid with the formula MM12 or MM16 (*J. Gene Med*; 2002; 4; 415-427):

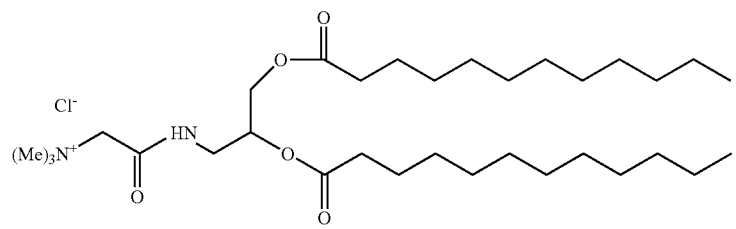

MM12

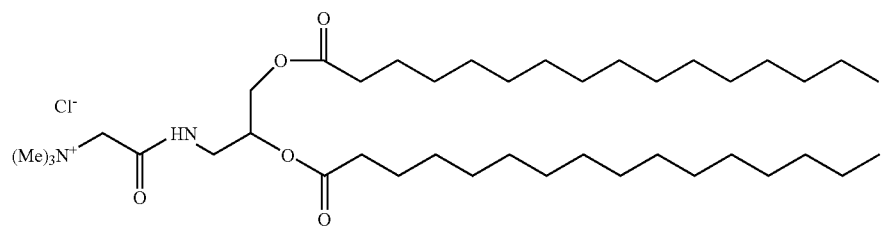

MM16

The fusogenic colipid may, for example, be dioleoylphosphatidylethanolamine (DOPE) or cholesterol.

The present invention also concerns the use of the liposomal compounds described above for the delivery, that is, the transmembrane transfer, of molecules of therapeutic interest and/or DNA or RNA.

Notably, the invention concerns the use of these liposomal compounds for the transmembrane transfer of genes.

The invention can be better understood with the following description of non-limiting examples given in relation to the drawings in which FIGS. 1 and 2 represent the influence of the plasmid (pCMVLuc) on the zeta potential and the size of the different complexes integrating liposomal compositions according to the invention.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

EXAMPLE 1

The Spacer with Formula (4)

Figure 1:
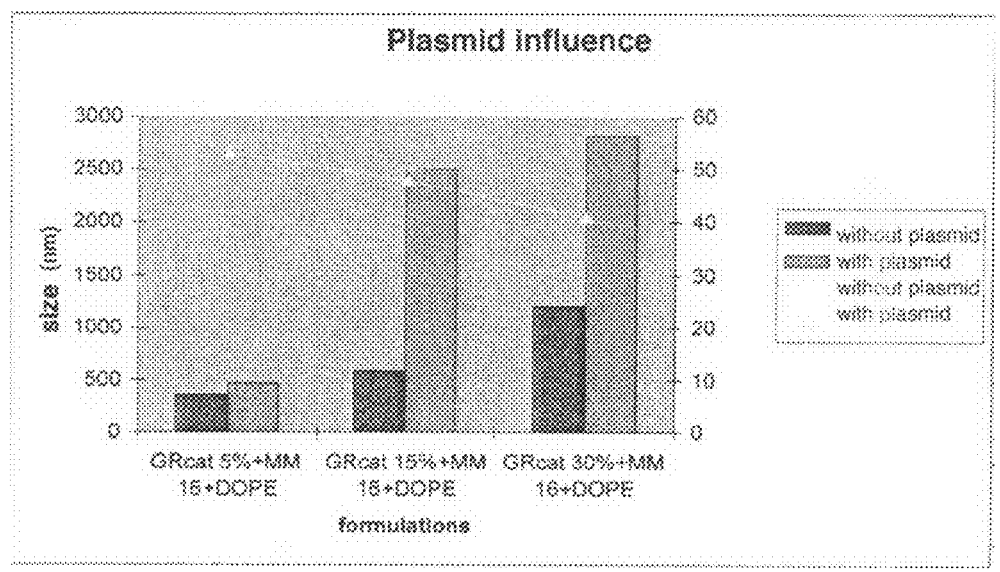
FIG. 1 is a graph that illustrates the influence of the plasmid (pCMVLuc) on the zeta potential and the size of the different complexes.

The diol (8) (500 mg; 3.85 mmol) is dissolved in 50 mL of anhydrous $CH_2Cl_2$ and the proton sponge (1.7 g; 2.6 eq) is added. The milieu is agitated for one hour at ambient temperature. Then the triflate (9) is slowly added (4.4 g; 2.6 eq) and the mixture is brought to reflux for 2 days. After cooling, the reaction is filtered to eliminate the proton sponge salts. The $CH_2Cl_2$ is concentrated in a vacuum.

The dibenzylated product obtained is purified on a silica gel column (eluent: ethyl acetate-petroleum ether 95/5 v/v) and 1.92 g of white solid is recuperated (yield: 74%).

The dibenzylated product thus prepared (2.6 g; 4 mmol) is solubilised in 100 mL of cyclohexane and palladium acetate is added (150 mg; 5% mass). The milieu is placed under a hydrogen atmosphere and agitated for 5 hours. Then the milieu is heated until the product is entirely dissolved and hot filtered on celite and concentrated under a vacuum. The solid is heat solubilised in cyclohexane; after cooling the product is recuperated by filtration on a Buchner funnel. Thus, 1.7 g of compound (4) is recuperated, in the form of a white solid (yield: 90%).

EXAMPLE 2

Spacer with Formula (3)

To a suspension of phosphonium salt (6) (300 mg; 0.34 mmol) in 6 mL of anhydrous THF, at 0° C., butyllithium in solution in hexane (2M) (360 µL; 0.72 mmol; 2.1 eq) is added; an orange colour appears. The reaction milieu is agitated for 15 minutes at 0° C., then the aldehyde (7) (Y is a benzyl) (239 mg; 0.69 mmol; 2.0 eq) in solution in 6 mL of anhydrous THF is added dropwise via cannula. Progressive decoloration is observed as well as the formation of a precipitate. After a few minutes, the excess butyllithium is destroyed by water. The mixture is extracted three times with the mixture EP/AcOEt (6/4 v/v) then the organic phases are washed with water, dried, filtered and concentrated. Silica gel column chromatography (25 eq, eluent: EP/AcOEt (99/1 v/v)) results in the isolation of 150 mg of unsaturated spacer (0.21 mmol) in the form of a white solid (yield: 63%).

The benzylated product (1.93 g; 2.8 mmol) is solubilised in ethanol (150 mL) then palladium on active carbon is added (500 mg). The reaction mixture is placed under a hydrogen atmosphere for one night. The reaction milieu is slightly heated and then heat filtered on celite, and the solvent is evaporated. One obtains 1.34 g (2.6 mmol) of product (3) in the form of a white solid (yield: 93%).

EXAMPLE 3

Compound with Formula (2)

The 2,6-lutidine (425 µL: 3.8 eq) then 20 mL of anhydrous dichloromethane are added into a dry round-bottomed flask. At 0° C., the triflic anhydride (600 µL; 3.8 eq) is added and the mixture is agitated for 15 minutes at ambient temperature. The diol (4) (500 mg; 1 mmol) in solid form is added all at once. After a few minutes water is added and the aqueous phase is extracted 3 times with dichloromethane. The organic phases are collected, washed with an aqueous solution of 5% hydrochloric acid, then an aqueous solution of 5% sodium bicarbonate and finally with a saturated solution of sodium chloride. The organic phase is dried on $MgSO_4$, filtered and concentrated. The product is rapidly purified, because it is unstable, by silica gel column chromatography (eluent: EP/Ac OEt (8/2 v/v). The ditriflate thus obtained (Rf 0.8 (EP/AcOEt 8/2 v/v)) is immediately placed under reaction.

At O° C., the alcohol (5) (Y is a benzyl) (1.5 g; 3 eq) dissolved in 6 mL of anhydrous THF is added to a suspension of potassium hydride (568 mg; 4 eq), in suspension in 6 mL of anhydrous THF. The reaction mixture is agitated for 30 minutes at ambient temperature. The triflate (800 mg; 1.05 mmol; 1 eq) dissolved in 8 mL of anhydrous THF is added dropwise. After 2 hours, the excess potassium hydride is destroyed by water. Ethyl ether extraction is done. The organic phase is dried on magnesium sulphate and then filtered and concentrated. Purification by silica gel column chromatography (40 eq, eluent: EP/AcOEt (99/1 v/v)) results in the isolation of 23 mg (0.45 mmol) of benzylated compound in the form of a colourless oil (yield 45% (for the two steps)).

The product thus prepared (623 mg; 0.45 mmol) is solubilised in 10 mL of ethyl acetate and the palladium acetate is added (30 mg; 5% mass). The milieu is placed under a hydrogen atmosphere and agitated for 24 hours. The reaction milieu is then filtered on celite and concentrated under a vacuum. Thus, 463 mg of compound (2) is recuperated which is also in the form of a colourless oil (yield: 85%).

EXAMPLE 4

Compound with Formula (1)

Into a very dry round-bottomed flask, the 2,6-lutidine (423 µL; 3.60 mmol; 3.8 eq), 20 mL of anhydrous dichloromethane and, at 0° C., the triflic anhydride (611 µL; 3.60 mmol; 3.8 eq)

are added. After 10 minutes of agitation at 0° C., the diol (3) (500 mg; 0.96 mmol) in solid form is added all at once. The reaction mixture is brought to ambient temperature then heated to 30° C.: the diol dissolves. After a few minutes, after the addition of water, the aqueous phase is extracted 3 times with dichloromethane. The organic phases are collected, washed with an aqueous solution of 5% hydrochloric acid, then an aqueous solution of 5% sodium bicarbonate and finally with a saturated solution of sodium chloride. The organic phase is dried, filtered and concentrated. The product is rapidly purified by silica gel column chromatography (20 eq eluent: EP/AcOEt (9/1 v/v)). The triflate thus obtained, in the form of a white solid, is immediately placed under reaction.

At 0° C., the triflate previously described (750 mg; 0.96 mmol; 1 eq) in 6 ml of anhydrous THF is added dropwise to a suspension of potassium hydride (438 mg; 3.8 mmol; 4 eq) and alcohol 5 (1.32 g; 2.87 mmol; 3 eq in 12 mL of anhydrous THF. The reaction mixture is agitated for 10 minutes at 0° C. After a few minutes, after the addition of water, diethyl ether extraction is done. The organic phase is dried on magnesium sulphate and then filtered and concentrated. Purification by silica gel column chromatography (40 eq eluent: EP/AcOEt (1/0 then 95/5 v/v) results in the isolation of the pseudo-macrocyclic benzylated product (860 mg; 0.61 mmol) which is in the form of a yellowish oil (yield: 64% (2 steps)).

The dibenzylated hemi-macrocyclic diol (1.77 g; 1.2 mmol), solubilised in ethyl acetate (50 mL), is put under a hydrogen atmosphere for one night, in the presence of palladium on active carbon (500 mg). Hot filtration on celite is done and the compound (1) (1.2 g; 0.97 mmol), in the form of an oil, is isolated after concentration under reduced pressure (yield: 80%).

EXAMPLE 5

Liposomal Compositions

Different liposomal compositions B, C, D, E, and E1 have been prepared by hydration of a lipid film by a solution containing 2.5% carboxyfluorescein. After hydration of the lipid films constituted of a mixture of pure lipids or synthetic lipids, then agitation of the solution for a few hours, the samples were extruded across a polycarbonate membrane (400 nm then 200 nm). Filtration on a Sephadex G75 gel allowed for collection of the liposomal compositions.

The stability of these different liposomal compositions according to the invention has been tested at a temperature of 37° C.:

in the presence of a surfactant compound (aqueous solution of 0.4% sodium cholate) in order to model the behaviour of these compositions in the presence of bile salts (test No. 1);

in the presence of lipoprotein rich calf serum in order to model the behaviour of these compositions in the blood milieu (test No. 2);

in an acid milieu, at pH 2-3 (1XKRB buffer), in order to mimic the behaviour of these compositions in the stomach (test No. 3).

These tests are based on the determination by spectrofluorometry of the rate of release of an encapsulated fluorescent probe. In the first two cases, the release of the fluorescent probe was measured by spectrofluorometry. For the study as a function of pH, after incubation, the pH is neutralised and dialysis of the free carboxyfluorescein is done. The liposomes are thus lysed on the carboxyfluorescein remaining encapsulated is measured.

The results obtained are given in tables 1 to 3 below in reference to a liposomal composition A containing only phosphatidylcholine from egg lecithin (EPC).

Results of Test No. 1 (in the Presence of Surfactant).

Table 1 below gives the results obtained from test No. 1 with different liposomal compositions.

TABLE 1

| Liposomal composition | Compound according to the invention | Content (in mass) | Colipid | Content (in mass) | % release |
|---|---|---|---|---|---|
| A | None | 0 | EPC* | 100 | 100 |
| B | Of formula 1 | 20 | EPC | 80 | 50 |
| C | Of formula 1 | 30 | EPC | 70 | 30 |
| D | Of formula 1 with X = 1 Z = $CH_2$ and R1 = R2 = β-lactosyl | 60 | EPC | 40 | 40 |

These results show that the compounds of the present invention indicated in the second column of table 1 give liposomal compositions B, C, and D increased stability in the presence of a surfactant compound, which tends to prove that the compositions according to the invention will present increased stability in the presence of bile salts.

It was also observed that the synthetic compounds incorporated into certain formulations lead to better stability than the natural macrocyclic diols (diglycerol tetraether—DGTE) obtained after hydrolysis of the polar heads.

Results of Test No. 2 (in the Presence of Calf Serum)

Table 2 below gives the results obtained with test No. 2 with different liposomal compositions.

TABLE 2

| Liposomal composition | Compound according to the invention | Content (in mass) | Colipid* | Content (in mass) | % release |
|---|---|---|---|---|---|
| A | None | 0 | EPC* | 100 | 100 |
| E | Of formula 1 with X = 1 Z = $CH_2$ and R1 = R2 = phosphatidyl choline | 100 | none | | 30 |
| E1 | Of formula 1 with X = 1 Z = $CH_2$ and R1 = R2 = phosphatidyl choline | 60 | EPC | 40 | 60 |
| D | Of formula 1 with X = 1 Z = $CH_2$ and R1 = R2 = β-lactosyl | 60 | EPC | 40 | 40 |

These results show that the compounds of the present invention indicated in the second column of table 2 give liposomal compositions D, E, and E1 increased stability in the presence of calf serum, rich in lipoproteins, which tends to prove that the compositions according to the invention will present increased stability in the blood milieu.

Results of Test No. 3 (in Acid Milieu)

Table 3 below gives the results obtained with test No. 3 with different liposomal compositions.

TABLE 3

| Liposomal composition | Compound according to the invention | Content (in mass) | Colipid* | Content (in mass) | % release** |
|---|---|---|---|---|---|
| A | None | 0 | EPC* | 100 | 95 |
| E | Of formula 1 with X = 1 Z = CH$_2$ and R1 = R2 = phosphatidyl choline | 100 | none | | 30 |
| E1 | Of formula 1 with X = 1 Z = CH$_2$ and R1 = R2 = phosphatidyl choline | 60 | EPC | 40 | 85 |

**after 10 minutes of incubation

These results show that the compounds of the present invention indicated in the second column of table 3 increase the stability of liposomal compositions in acid pH, which tends to prove that the compositions according to the invention will present increased stability in the stomach. This stability is comparable (20-30% release) to that obtained with natural lipid extracts of *Thermoplasma acidophilum* (a thermoacidophilic species with double tolerance to high temperatures and low pH).

EXAMPLE 6

Delivery

Different liposomal compositions according to the present invention have also been made in order to test their ability to deliver the pCMVLuc plasmid.

The compound with the general formula (1) used in these compositions is that in which X=0, or 1 Z=O or CH$_2$ and in which R$_1$=R$_2$=NHC(O)CH$_2$N$^+$Me$_3$, Cl. This compound is hereafter referred to as GRcat.

This compound has been associated with a mixture of colipids constituted of equal parts of dioleoylphosphatidylethanolamine (DOPE) or cholesterol (Chol) on one hand and two-chain cationic lipid MM16 on the other hand.

The details of these liposomal compositions are given in table 4 below.

TABLE 4

| Composition | Compound according to the invention | Content (mass) | Colipids | Content (mass) |
|---|---|---|---|---|
| F1 | GRcat | 5% | DOPE + MM16 | 95% |
| F2 | GRcat | 15% | DOPE + MM16 | 85% |
| F3 | GRcat | 30% | DOPE + MM16 | 70% |
| F4 | GRcat | 5% | Chol + MM16 | 95% |
| F5 | GRcat | 15% | Chol + MM16 | 85% |
| F6 | GRcat | 30% | Chol + MM16 | 70% |

Dynamic light scattering measurements (determination of the size of particles) and the zeta potential (evaluation of the overall charge ratio of particles) have also allowed for the determination of the size and the overall charge ratio of these different liposomal compositions before and after adding pCMVLuc plasmid.

Figure 2:
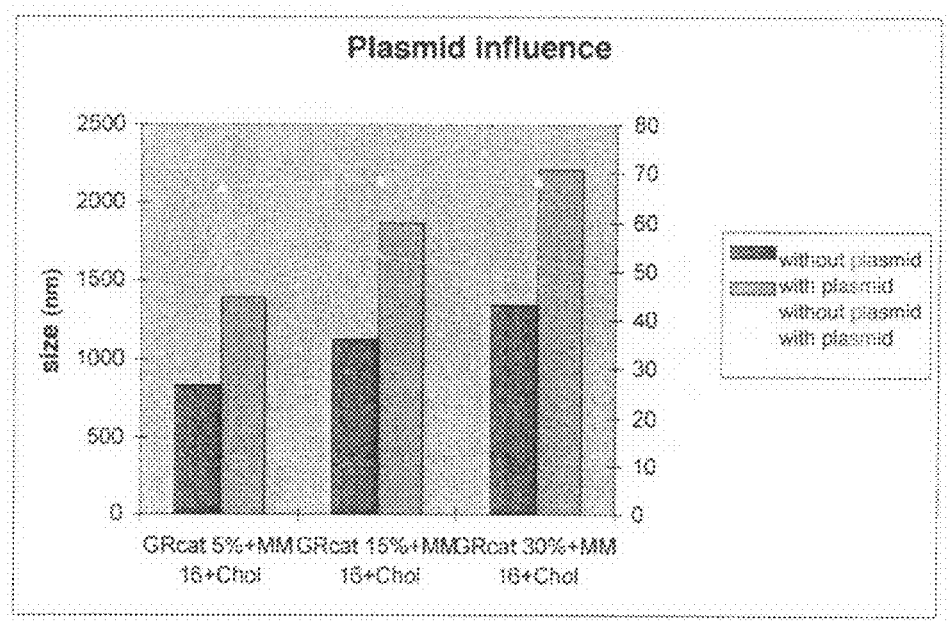
FIG. 2 is a graph that illustrates the influence of the plasmid (pCMVLuc) on the zeta potential and the size of the different complexes.

The results obtained are given in FIGS. 1 and 2, attached.

These results show the formation of supramolecular aggregates from the electrostatic interaction between the cationic vesicles and the plasmid (pCMVLuc).

In fact, after adding plasmid, one observes an increase in the size of particles with a parallel reduction of the overall charge ratio which nevertheless remains positive; a potential positive zeta after complexing the plasmid is necessary in the framework of delivery without targeting agent because the internalisation of the aggregates is done by electrostatic interaction between the cell membrane (negatively charged) and the vesicle (positively charged).

It seems that an increase in the rate of incorporation of the GRcat compound according to the present invention leads to an increase in the size of the liposomes and an increase (even more important) in the size of the DNA-liposome complexes.

The increase in the rate of incorporation does not have a significant effect on the value of the zeta potential however, the formation of supramolecular aggregates with DNA leads to a decrease in zeta potential.

The liposomal compositions according to the present invention, the size and zeta potential of which can be controlled, thus constitute systems that may be used for the delivery of DNA and RNA molecules and notably of genes.

The in vitro transfection studies carried out using formulations incorporating the dicationic type 1 tetraethers (R$_1$=R$_2$=NH(CO)—CH$_2$—N$^+$(CH$_3$)$_3$; x=0 and Z=O or X=1 and Z=CH$_2$), and the DOPE or the cholesterol as colipid, for 4 μg of DNA delivered (pEGFP-N1 plasmid encoding for the GFP protein under the control of the cytomegalovirus promoter, pCMV), on A549 cells (type II human alveolar epithelial cells), at different charge ratios (R(+/−)=0.5; 1; 2; 4; 8)), have shown that low quantities of colipids (DOPE or cholesterol) are sufficient to assure good transfection efficacy.

In fact, the best results are obtained with the formulations using the tetraether 1 (R$_1$=R$_2$=NH(CO)—CH$_2$—N$^+$(CH$_3$)$_3$; x=0 and Z=O) as a cationic lipid in the presence of DOPE. A very high efficacy (90% of cells living and transfected) is obtained for 5% or 15% DOPE and for R (+/−)=8.

Figure 3:
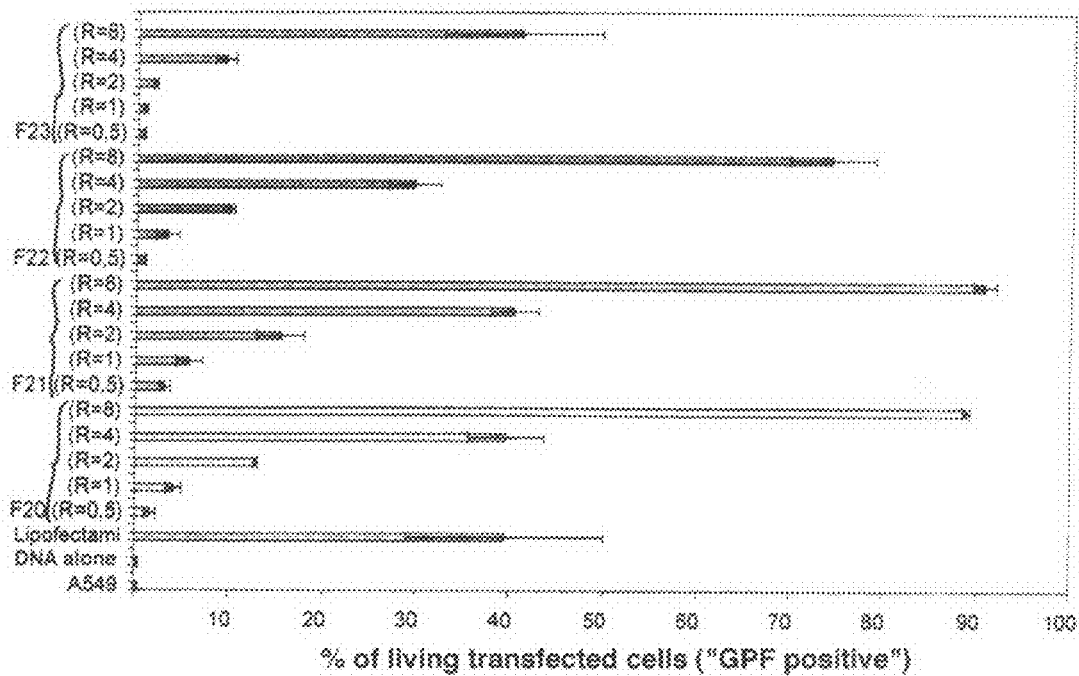
FIG. 3 illustrates the % of living transfected cells ("GFP positive").

FIG. 3 shows the transfection efficacy of type 1 tetraether formulations (R1=R2=NH(CO)—CH$_2$—N$^+$(CH$_3$)$_3$; x=0 and Z=O)/DOPE on A549 cells for 4 μg of DNA delivered.

On this figure "Lipofectami" corresponds to Lipofectamine (reference commercial cationic lipid).

R represents the charge ratio (+/−).

F20 indicates 5% DOPE, F21 15% DOPE, F22 30% DOPE and F23 50% DOPE.

In the case of tetraether 1 (R1=R2=NH(CO)—CH$_2$—N$^+$(CH$_3$)$_3$; x=1 and Z=CH$_2$), maximum efficacy begins to be observed with formulations incorporating 15% DOPE for a charge ratio R (+/−) under 4 (82% of cells living and transfected). When the charge ratio increases, no efficacy is observed with compound 1 (R1=R2=NH(CO)—CH$_2$—N$^+$(CH$_3$)$_3$; x=1 and Z=CH$_2$). This observation may be explained, in this case, by too much internalisation of lipid/DNA complexes. The entry of a high quantity of lipids in into the cells leads to destabilisation of the cell membranes and consequently to a high level of mortality.

Figure 4:
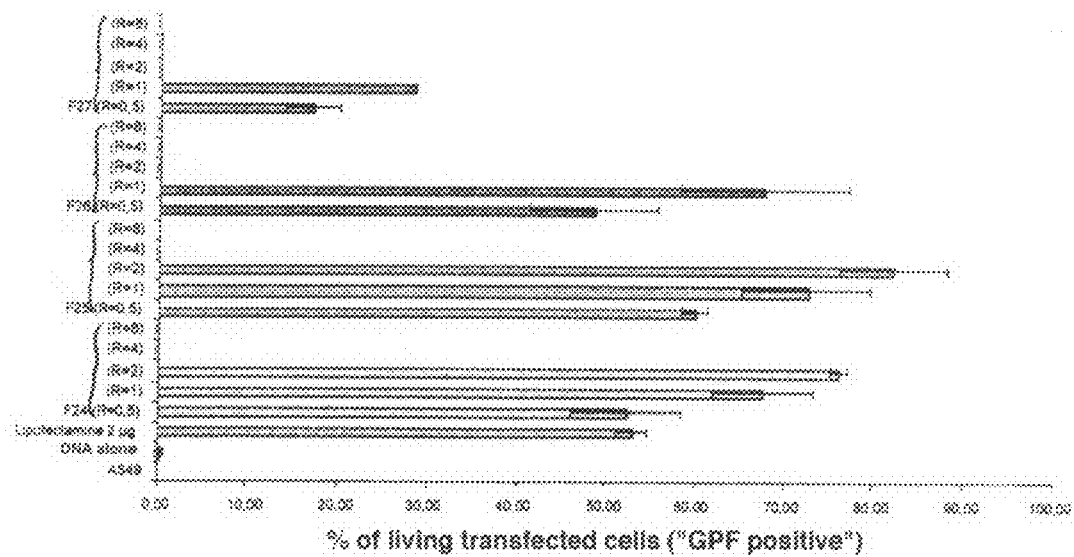
FIG. 4 illustrates the % of living transfected cells ("GFP positive").

FIG. 4 shows the transfection efficacy of tetraether 1-type formulations (R$_1$=R$_2$=NH(CO)—CH$_2$—N$^+$(CH$_3$)$_3$; x=1 and Z=CH$_2$)/DOPE on A549 cells for 4 μg of DNA delivered.

The reference is also Lipofectamine.

R represents the charge ratio (+/−).

F24 indicates 5% DOPE, F25 15% DOPE, F26 30% DOPE and F27 50% DOPE.

These results clearly show the high potential of these cationic tetraethers for the transfer of genes.

The invention claimed is:

1. A compound with the general formula (1):

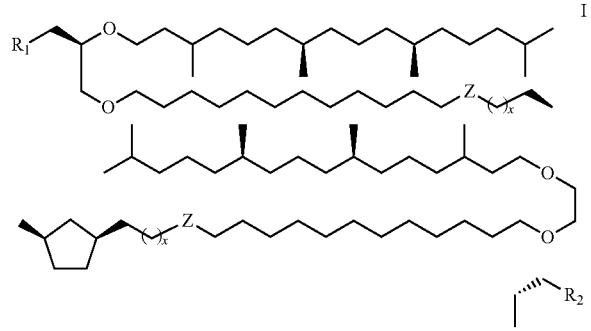

in which:

X is equal to zero or one;

Z represents an O, an S or a $CH_2$, $R_1$ and $R_2$, which can be identical or different, represent one of the following substituents:

OH

OY with Y representing a protector group;

$OR_3$, $R_3$ representing a monosaccharide or disaccharide substituent;

$A_1$-$CH_2$—$N^+(CH_3)_3 X^-$, X representing a halogen, $A_1$ representing an amide (NHC(O)) or ester (OC(O)) bond;

$OPO(OM)_2$, M representing an alkaline metal cation or alkaline-earth metal;

$OP(O)O^-$—$O(CH_2)_2$—$N^+(CH_3)_3$, $A_2$-$(PEG_{X1}$-$A_3)_n$-$R_4$, n being equal to 0 or 1, $PEG_{X1}$ being a polyethyleneglycol of molecular weight $X_1$, $X_1$ being less than or equal to 5,000 daltons, $A_2$ and $A_3$ being identical or different and representing one ether (O), ester (OC(O)), amide (NHC(O)), urea (NHC(O)NH), thiourea (NHC(S)NH), or thioether (S) bond, $R_4$ representing a targeting agent.

2. The compound according to claim 1 wherein said protector group is selected from the group consisting of: an allyl, a benzyl, a tetrahydropyranyl, a trialkylsilyl group, and a combination thereof.

3. The compound according to claim 1 wherein said targeting agent is selected from the group consisting of: folic acid, multi-antenna structures comprising several $R_3$ motifs, antibodies, peptides, and a combination thereof.

4. The compound according to claim 1 wherein $R_3$ is a substituent selected from the group consisting of: D-galactosyl, D-glucosyl, D-mannosyl, lactosyl, maltosyl substituents, and a combination thereof.

5. The compound according to claim 1 wherein x is equal to zero or one;

Z represents an O or a $CH_2$;

$R_1$ and $R_2$ are identical or different and represent one of the following substituents:

OH $OR_3$, $R_3$ representing a lactosyl;

$OP(O)O^-$—$O(CH_2)_2$—$N^+(CH_3)_3$;

$OPO(OM)_2$, M representing a metal cation or alkaline-earth metal;

$A_1$-$CH_2$—$N^+(CH_3)_3 X^-$, X representing a halogen, $A_1$ representing an amide (NHC(O)) or ester (OC(O)) bond.

6. The compound according to claim 5 wherein $R_1$=$R_2$=$OR_3$, $R_3$=β-lactosyl.

7. The compound according to claim 1 wherein $R_1$=$R_2$=$OP(O)O^-$—$O(CH_2)_2$—$N^+(CH_3)_3$.

8. The compound according to claim 1 wherein $R_1$=$R_2$=$NHC(O)CH_2$—$N^+(CH_3)_3 X^-$, X represent a halogen.

9. The compound according to claim 8 wherein X is chlorine or bromine.

10. The compound according to claim 1 wherein the compound is of formula (1):

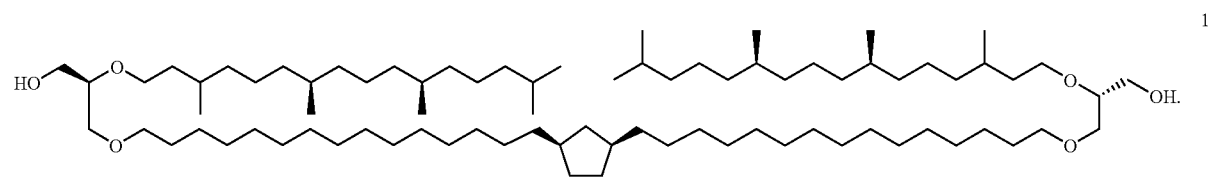

11. The compound according to claim 1 wherein the compound is of formula (2):

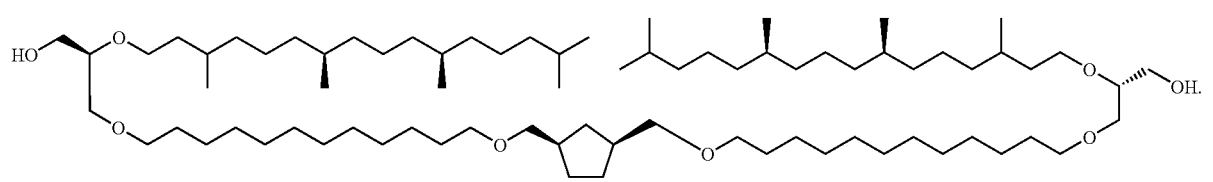

12. A composition comprising: a liposomal composition comprising at least one compound according to claim 1.

13. The composition according to claim 12 further comprising at least one colipid.

14. The composition according to claim 13 wherein said colipid is phosphatidylcholine from egg lecithin.

15. The composition according to claim 13 further comprising a compound with the general formula I in which $R_1$ and $R_2$ are identical or different and represent one of the following motifs:
- $A_1$-$CH_2$—$N^+(CH_3)_3 X^-$, X representing a halogen, $A_1$ representing an amide (NHC(O)) or ester (OC(O)) bond;
- $A_2$-$(PEG_{X1}$-$A_3)_n$-$R_4$, n being equal to 0 or 1, $PEG_{X1}$ being a polyethyleneglycol of molecular weight $X_1$, $X_1$ being less than or equal to 5,000 daltons, $A_2$ and $A_3$ being identical or different and representing one ether (O), ester (OC(O)), amide (NHC(O)), urea (NHC(O)NH), thiourea (NHC(S)NH), or thioether (S) bond, $R_4$ representing a targeting agent, and at least one cationic colipid
and at least one fusogenic colipid.

16. The composition according to claim 15 wherein said cationic colipid is an MM12 or MM16 two-chain cationic lipid.

17. The composition according to claim 15 wherein said fusogenic colipid is dioleoylphosphatidylethanolamine or cholesterol.

18. A method of delivering molecules of therapeutic interest using the liposomal composition according to any one of claims 12 to 17 for delivery of molecules of therapeutic interest, and having the following steps:
a) preparing a complex made of said molecule of therapeutic interest and said liposomal composition according to any one of claims 12 to 17, comprising the steps of:
  diluting said molecule of therapeutic interest in a sterile solution containing glucose at the desired concentration,
  mixing said liposomal composition according to any one of claims 12 to 17 with the dilution of said molecule of therapeutic interest obtained in the previous step in order to form the complex, and
b) injecting said complex of step a), warmed at room temperature, in a vein of a mammal.

19. The method according to claim 18, wherein the molecules of therapeutic interest include DNA or RNA molecules.

20. A compound of formula (3):

suitable for the synthesis of the compound according to formula (1).

21. A compound of formula (4):

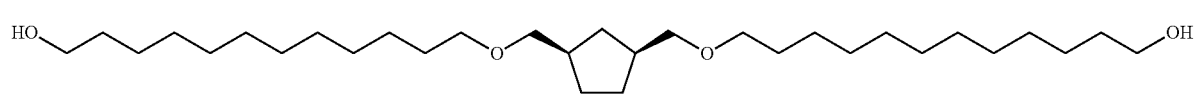

suitable for the synthesis of the compound according to formula (2).

* * * * *